(12) United States Patent
Sides et al.

(10) Patent No.: US 7,780,842 B2
(45) Date of Patent: Aug. 24, 2010

(54) APPARATUS AND METHOD FOR DETERMINING THE ZETA POTENTIAL OF SURFACES FOR THE MEASUREMENT OF STREAMING METRICS RELATED THERETO

(75) Inventors: Paul J. Sides, Pittsburgh, PA (US);
James D. Hoggard, Carnegie, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 723 days.

(21) Appl. No.: 11/629,236

(22) PCT Filed: Jun. 10, 2005

(86) PCT No.: PCT/US2005/020618

§ 371 (c)(1),
(2), (4) Date: Dec. 11, 2006

(87) PCT Pub. No.: WO2005/124335

PCT Pub. Date: Dec. 29, 2005

(65) Prior Publication Data

US 2008/0264795 A1  Oct. 30, 2008

Related U.S. Application Data

(60) Provisional application No. 60/579,125, filed on Jun. 11, 2004, provisional application No. 60/656,313, filed on Feb. 25, 2005.

(51) Int. Cl.
*G01N 27/26* (2006.01)
(52) U.S. Cl. .................... 205/790.5; 205/775; 204/400; 204/409; 324/453
(58) Field of Classification Search .............. 204/400, 204/409; 205/775, 790.5; 324/453; 422/82.01
See application file for complete search history.

(56) References Cited

U.S. PATENT DOCUMENTS 4,595,462 A * 6/1986 Vangaever et al. ........ 205/793.5

(Continued)

FOREIGN PATENT DOCUMENTS

EP    0811665 A2    12/1997

(Continued)

OTHER PUBLICATIONS

PCT "Notification of Transmittal of the International Search Report and the Written Opinion of the International Searching Authority, or the Declaration" for PCT/2005/044385.

(Continued)

*Primary Examiner*—Kaj K Olsen
(74) *Attorney, Agent, or Firm*—Fox Rothschild LLP

(57) ABSTRACT

Methods and apparatuses for measuring streaming metrics. A method for measuring a streaming metric corresponding to a rotating surface is characterized by rotating the surface around an axis of rotation and measuring the streaming metric at a location within one radius from the axis of rotation and within three radii from the surface, wherein the location does not contact the surface. Apparatus for measuring a streaming metric corresponding to a rotating surface are characterized by a working electrode which does not contact the surface, a counter electrode, a meter connected to the working electrode and the counter electrode, a rotatable spindle on which the surface is mounted, and a container for holding electrolyte, wherein the working electrode, counter electrode, and surface are located within the container.

17 Claims, 12 Drawing Sheets

U.S. PATENT DOCUMENTS

| | | | |
|---|---|---|---|
| 5,858,813 | A | 1/1999 | Scherber et al. |
| 6,676,766 | B2 | 1/2004 | Harano et al. |
| 6,736,992 | B2 | 5/2004 | Zhang et al. |

FOREIGN PATENT DOCUMENTS

| | | | |
|---|---|---|---|
| EP | 0811665 | A3 | 10/1998 |

OTHER PUBLICATIONS

PCT "International Search Report" for PCT/US2005/044385.

PCT "Written Opinion for the International Searching Authority" for PCT/US2005/044385.

J.D. Hoggard, P.J. Sides, D.C. Prieve, "Measurement of the Streaming current near a Rotating Disk to Determine its Zeta Potential", LANGMUIR, vol. 21, Jul. 6, 2005, pp. 7433-7438, XP002380779.

P.J. Sides, J.H. Hoggard, "Measurement of the Zeta Potential of Planar Solid Surfaces by Means of Rotating Disk", LANGMUIR, vol. 20, Nov. 24, 2004 pp. 11493-11498, X66516P002380780.

PCT International Search Report and Written Opinion of the International Search Authority, Intl. App. No. PCT/US2005/020618, Mailed Oct. 5, 2005.

Notification of Transmittal of the International Preliminary Report on Patentability, Intl. App. No. PCT/US2005/020618, Mailed May 30, 2006.

Corrected Notification of Transmittal of the International Preliminary Report on Patentability, Intl. App. No. PCT/US2005/020618, Mailed Sep. 22, 2006.

Knodler, R; Kohling, A; Walter, G; "Measuring Streaming Potentials on Flat Surfaces with Rotating Electrodes", Journal of Electroanalytical Chemistry and Interfacial Electrochemistry, vol. 56, 1974, pp. 315-319, XP002346287.

Zimmerman, R, et al.; "Bestimmung des zeta-potentials und der grenzflaechenleitfaehigkeit durch stroemungspontential-und stroemungsstrommessungen determination of the zeta potential and the surface conductivity by streaming potential and streaming current measurements", Technisches messen tm, R. Oldenbourg Verlag. Munchen, DE, vol. 67, No. 9, Sep. 2000 pp. 353-360, XP001132480 ISSN: 0171-8096.

Soong, C. Y.; Wang, S. H.; "Analysis of rotation-driven electrokinetic flows in microscale gap regions of rotating disk systems", Journal of Colloid and Interface Science, vol. 269, No. 2, Jan. 15, 2004, pp. 484-498, XP002346288.

Knodler, R and Langbein, D; "Zeitschrift fur Physikalische Chemie Neue Folge." ("Determination of the Charge Distribution in Front of a Rotating Electrode"), Bd. 98 S., pp. 421-434 (1975), Battelle-Institut, 6 Frankfurt/Main 90, Am Romerhof 35.

Sidorova, M. P.; Fridrikhsberg, D. A.; Kibirova, N. A.; "Issledovanie elecktrokineticicheskogo potenziala metodom potenziala techenja na vrashajushemsja diske", Vestnik Leningradskogo Universiteta, vol. 2, pp. 121-123 (1973), XP009066516.

* cited by examiner

APPARATUS AND METHOD FOR DETERMINING THE ZETA POTENTIAL OF SURFACES FOR THE MEASUREMENT OF STREAMING METRICS RELATED THERETO

CROSS REFERENCE TO RELATED APPLICATIONS

This application claims priority from Patent Cooperation Treaty application number PCT/US2005/020618, filed Jun. 10, 2005, which claims priority from U.S. Provisional Patent Application No. 60/579,125, filed Jun. 11, 2004, and U.S. Provisional Patent Application No. 60/656,313, filed Feb. 25, 2005.

STATEMENT REGARDING FEDERALLY-SPONSORED RESEARCH AND DEVELOPMENT

This invention was made with government support under Grant Number CTS 0338089 awarded by the National Science Foundation. The United States government has certain rights in this invention.

BACKGROUND OF THE INVENTION

Zeta potential is an electric potential at the surface of shear relative to an electrically neutral solution far away and characterizes the apparent surface charge. Zeta potential may exist on a variety of surfaces including solids, such as particles or fibers, or planar surfaces. The term "surface", as used herein, will include these and other examples on which a zeta potential may exist.

Knowing the zeta potential of macroscopic solid surfaces is useful. For example, the zeta potential of silicon can determine whether particles from solution are more or less likely to stick to it. If the silicon wafer has a surface charge and the particles in solution are charged with the same sign, then particles have a lower tendency to adhere. In chemical-mechanical planarization of silicon wafers, particles adsorb to the surface during polishing due to the opposite zeta potentials of the surface and the polishing particles. After polishing, increasing the pH such that the wafer and particles both have a negative zeta potential can cause the particles and wafer to repel one another. The zeta potential of the silicon wafer can be measured to ensure the desorption of polishing particles. See, for example, U.S. Pat. Nos. 6,736,992 and 6,676,766.

As another example, the biocompatibility of polymers used in medical devices depends on the polymer's zeta potential. Measurements of zeta characterize the adsorption of proteins or surfactants to solid surfaces. See, for example, Hiemenz, P. C.; Rajagopalan, R., *Principles of Colloid and Surface Chemistry*, Marcel Dekker Inc.: New York, 1997; Shaw, D. J., *Introduction to Colloid and Surface Chemistry*, Butterworths: London, 1986; Lyklema, J., *Fundamentals of Interface and Colloid Science*, Academic Press: London, 1995: Vol. II; Hunter, R. J., *Zeta Potential in Colloid Science: Principles and Applications*, Academic Press: London, 1981; Werner, C.; Koerber, H.; Zimmermann, R.; Dukhin, S.; Jacobasch, H. J., *Journal of Colloid and Interface Science*, 1998, 208, 329; Sides, P. J.; Hoggard, J. D., *Langmuir* 2004, 20, 11493-11498; U.S. Pat. No. 6,736,992; and U.S. Pat. No. 6,676,766.

A prior art method for determining the zeta potential of planar surfaces is based on flow in a thin gap between parallel plates. Two identical plate samples, or two different plates where the zeta potential of one plate is known, form the gap. Pressure driven flow through the thin-gap cell moves the charge in the diffuse layer on each plate, thereby producing convected ionic current. One measures either a streaming potential difference or a streaming current between the inlet and outlet of the thin-gap cell by means of two Ag/AgCl electrodes connected to an external meter having either a high or low impedance, respectively. The zeta potential is proportional to the measured streaming potential or streaming current and can be calculated therefrom with the aid of known relationships and parameters. This approach has been incorporated into a commercial product. For example, Anton-Paar, a company based in Graz, Austria, manufactures a scientific instrument based on this design for determining the zeta potential of planar solids.

Despite advances in this field, prior art methods and apparatuses for determining zeta potential of solid surfaces suffer some disadvantages. The prior art methods require two surfaces to form a thin channel; hence both surfaces must be equivalent or the operator must subtract out the contribution of a common surface. Furthermore, not all planar materials, such as thin fibrous mats, are easily formed into or attached to rigid planar surfaces in such a way that they can sustain a tight seal against the pressures required to cause flow through a narrow gap.

Not all of the prior art suffers from the problem of having two surfaces in close proximity, but there are other deficiencies. Scientists (see M. P. Sidorova, D. A. Fridrikhsberg, N. A. Kibirova *Vestnik Leningradskogo Universiteta* Vol. 2 121-123 (1973) and references cited therein) used a thin film of liquid flowing over a rotating disk. This reference is in Russian, but as Applicant understands it, the reference electrodes used to detect the streaming potential were affixed to the surface of the disk. The means of rotation requires the disk to admit a spindle through it and requires a moving electrical connection between a meter and the wires leading to the reference electrodes, which can introduce noise in the electrical signal. Other methods for determining zeta potential have been proposed. For example, two scientists tried to make a streaming potential measurement with a rotating surface in contact with bulk solution (see R. Knodler, A Kohling, and G. Walter, "Measuring Streaming Potentials on Flat Surfaces with Rotating Electrodes," *Electroanal. Chem. and Interf. Electrochem.* 56 315-319 (1974). See also R. Knodler and D. Langbein *Zeitschriftfur Physikalische Chemie Neue Folge*. Bd. 98 S. 421434 (1975). See also R. Knodler and D. Langbein *Zeitschrift fur Physikalische Chemie Neue Folge*. Bd. 98 S. 421-434 (1975).). They made a ring of the desired material that was held between an axially concentric in-plane working electrode and an in-plane counter electrode. Their electrodes were integral to the disk and rotated with it. They measured the potential between two points (positions 2 and 3, in FIG. 1). Their method also required an aperture in the sample and also required a moving electrical connection. However, their method and experimental set-up failed to produce accurate results. In particular, they were not able to observe the 3/2 power dependence on the rotation rate expected on theoretical grounds and characteristic of this particular geometry. Experimenting with three different materials, they found exponents on the rotation rate of 0.27, 0.7, and 2.1. As a result, this new method fails to improve on the prior art.

Accordingly, there is a need by reason either of convenience or of feasibility for improved apparatuses and methods for determining zeta potential, particularly for apparatuses and methods for determining zeta potential of solid surfaces.

Those and other advantages of the present invention will be described in more detail hereinbelow.

BRIEF SUMMARY OF THE INVENTION

According to the present invention, the zeta potential of a surface can determined from a streaming metric (i.e., streaming current or streaming potential) corresponding to the rotating surface. The present invention describes a variety of ways to make such measurements, including making streaming potential or streaming current measurements near the surface with respect to suitable counter electrodes away from the surface. Although a disk-shaped surface is described in detail herein, it is also possible to measure the zeta potential of surfaces of arbitrary shape if suitable calibration is performed. For example, rotation of a square surface or a hemispherical surface would produce a measurable streaming potential that could be converted to zeta potential.

The present invention adds new theory, new apparatuses, and new methodology to the field of measuring zeta potential. The theory is extended by solving Laplace's equation in the bulk solution away from the surface of a disk-shaped surface, which allows mathematical connection of the streaming potential at any position in the vicinity of the disk to the zeta potential of the disk's surface. The new theory points to a non-obvious placement of the detecting electrodes. Experimental results are presented to further illustrate the present invention.

According to one embodiment of the present invention, a disk for which the zeta potential is to be measured is placed in an ionically conductive medium. A working electrode may be located adjacent to the surface of the disk, but not in physical contact with it. The working electrode may be at the axis of rotation and immediately adjacent to the disk, or it may be at other locations, as described herein. The working electrode may be a long and narrow wire with exposure only at the tip, or it may have other shapes. The wire may be oriented parallel to the axis of the disk, or it may be oriented in other ways. A counter electrode, having the same or different shape as the working electrode, may be located away from the disk's surface. The counter electrode may be, for example, concentric with the axis of rotation of the disk or it may have other shapes and orientations. The counter electrode may be located away from the axis of rotation or near the axis of rotation. The distance between the electrodes and the disk may also vary.

Rotation of the disk causes a measurable potential difference between the working electrode and the counter electrode. In the case of a disk shaped surface, the potential difference increases with the 3/2 power of the rotation rate when the rotation creates laminar flow in the vicinity of the disk. At high rotation rates, rotation of the disk creates turbulent flow in the vicinity of the disk and a different exponent is expected on the rotation rate, but a streaming potential difference nevertheless can be measured.

According to another embodiment of the present invention, methods and apparatuses are taught for measuring streaming current, which allows the use of higher conductivity electrolyte. An experimental relationship between the zeta potential and the measured streaming current is found for several embodiments of the present invention.

Another embodiment of the present invention oscillates a disk back and forth around its axis with, for example, a mechanical oscillator. This action according to the present invention would raise the detected voltage by an exponent of 3/2 on the frequency of oscillation.

According to another embodiment of the present invention, the zeta potential of a rotating disk can be measured between two electrodes, where one electrode is located at or near the axis of rotation of the disk and at a distance from the surface of the disk of about 5% of the disk's radius with the other electrode being located away from the disk at a distance of approximately ten times the disk's radius.

Many variations are possible with the present invention, and the present invention will be described in terms of several embodiments and variations. These and other teachings, variations, and advantages of the present invention will become apparent from the following detailed description of the invention.

BRIEF DESCRIPTION OF THE SEVERAL VIEWS OF THE DRAWING

Embodiments of the present invention will now be described, by way of example only, with reference to the accompanying drawings for the purpose of illustrating the embodiments, and not for purposes of limiting the invention, wherein.

DETAILED DESCRIPTION OF THE INVENTION

Theory of the Streaming Potential in the Vicinity of a Disk-Shaped Surface

Figure 1:
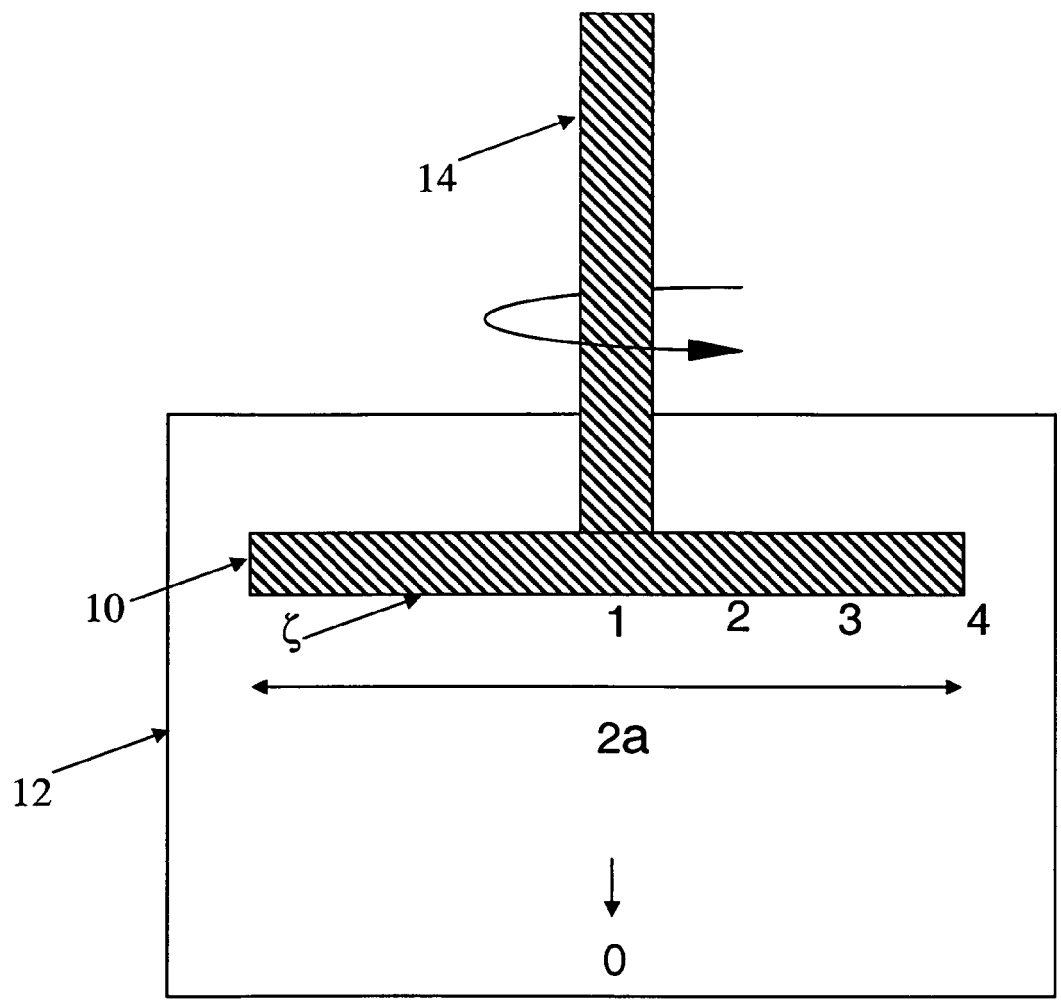
FIG. 1 is a diagram of a rotating disk and indicates four positions where electrodes have been placed on or near the disk's surface.

FIG. 1 illustrates an apparatus according to one embodiment of the present invention that includes a rotating disk surface 10 with radius $\alpha$ and zeta potential $\zeta$ on its surface. The apparatus also includes a container 12 holding electrolyte and a rotatable spindle 14 on which the disk 10 is mounted. The disk may be attached to the spindle in a variety of ways including, but not limited to, adhesion, mechanical attachment (such as clamping or screwing), magnetic attachment, or action of a vacuum created in the spindle 14 behind the disk 10. The disk 10 and spindle 14 rotate around an axis of rotation that passes through the disk 10 and the spindle 14. FIG. 1 also illustrates five locations (0, 1, 2, 3, and 4) relative to the surface of the disk 10 which will be referenced below with regard to measurements.

Although the present invention will be described in terms of a "disk", the present invention may also be used with non-disk-shaped surfaces. Furthermore, as used herein, the term "radius" and "radii" mean radial distance from the axis of rotation to the edge of the disk or other surface. In the case of a disk centered on the axis of rotation, the radius is equal in all directions across the surface. In the case of surfaces, such as non-circular surfaces or circular surfaces which are not centered on the axis of rotation, the radius may include two or more distances from the axis of rotation to the edges of the surface. The two or more distances may be discrete values, such in the case of a step change in distance, or the distances may be a range of distances, such as in the case of a smoothly varying non-circular shaped surface.

Figure 2:
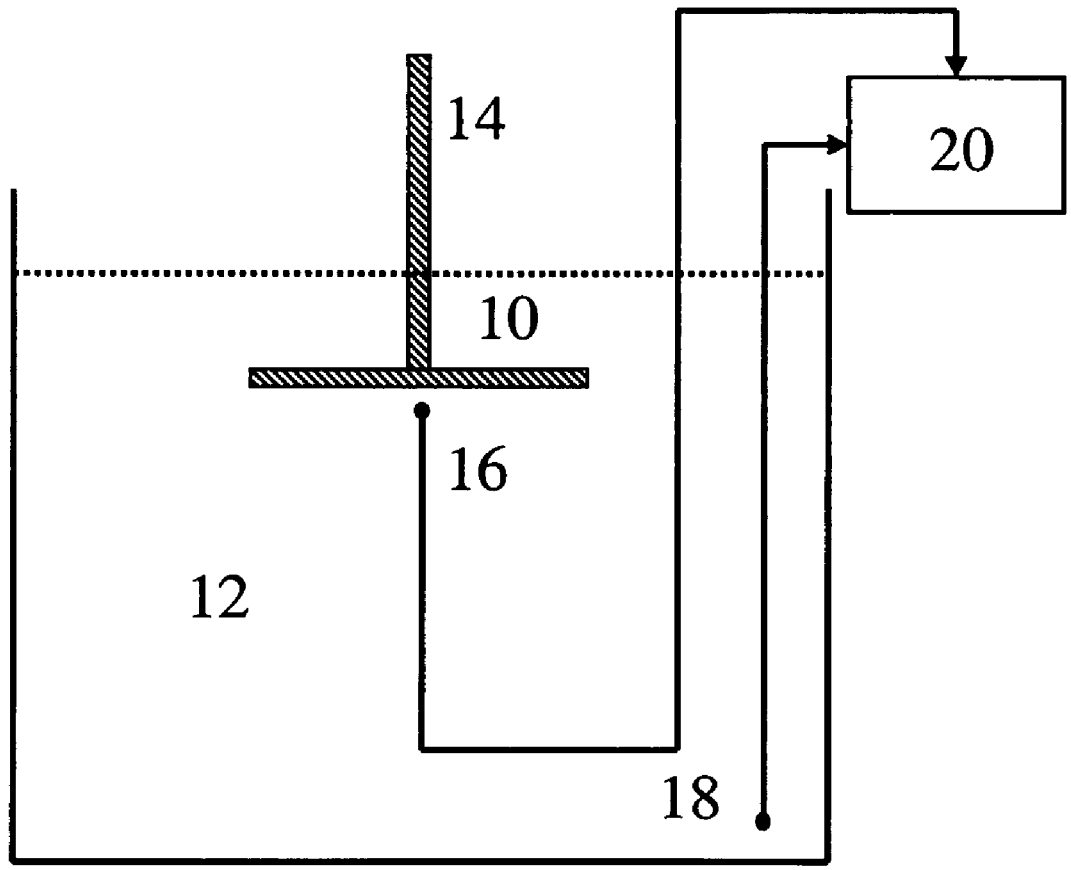
FIG. 2 is a schematic illustrating one embodiment of a streaming potential measurement apparatus.

FIG. 2 shows more detail of the apparatus, including a working electrode 16, and counter electrode 18, and a meter 20. The meter 20 may be a general purpose meter, such as one that can measure current, voltage, and perhaps other characteristics. In other embodiments, the meter 20 may be a special purpose meter, such as one that only measures current, or one that only measures voltage. In other embodiments, the meter 20 may be a system, such as a metering system or a measurement system. The meter 20 may be self contained, or it may be part of another device or system which performs measurements described herein. The meter 20 may also perform functions other than measurement, such as recording and analysis of data, or the meter 20 may be part of another device or system which performs functions in addition to measurement. For example, the meter 20 may include or be connected to an analog to digital converter and a processor or computer which may be used, for example, to collect and analyze measurement data. The processor or controller may also be used to operate and control some or all aspects of the present invention. As described in more detail hereinbelow, the apparatus illustrated in FIGS. 1 and 2 may be used to measure zeta potential.

Rotation of a disk 10 in a solution of aqueous electrolyte produces a streaming potential. The moving disk 10 generates radial flow with a velocity proportional to the radial distance from the axis. If the disk 10 surface is charged, radial convection along the disk 10 surface transports mobile unbalanced ionic charge in the diffuse ionic charge layer adjacent to the disk and thereby causes a sheet of electric current flowing outward along the disk 10 surface. The electrolyte medium provides a path for conduction of the current away from the disk 10. The sheet of current is thin with respect to the radius of the disk because the Debye length (as described below with respect to Equation [13]) is often on the order of one nm while practical surface sizes such as the disk 10 for this invention are greater than one millimeter.

Although the present invention will be generally described in terms of a disk 10 being rotated in one direction, the present invention may also be used with a disk 10 that is oscillated back and forth in alternating directions around its axis of rotation. This may be accomplished, for example, with a mechanical oscillator attached to the spindle 14 or with other devices. This oscillating action according to the present invention would raise the detected voltage by an exponent of 3/2 on the frequency of oscillation.

The viscosity and conductivity of the electrolyte in the container 12 are $\mu$ and $\kappa$, respectively. The potential in solution must satisfy Laplace's equation:

$$\nabla^2 \phi = 0 \quad [1]$$

Laplace's equation is separable and solvable in the semi-infinite domain where the origin is at the center of the disk 10. Using rotational elliptical coordinates, the solution is:

$$\phi = \sum_{n=0}^{\infty} B_n P_{2n}(\eta) M_{2n}(\xi) \quad [2]$$

where $\phi$ is electric potential that varies as a function of position in the semi-infinite domain and vanishes far from the disk 10. P represents Legendre polynomials of order 2n and M is a Legendre function of complex argument; it takes the value of unity on the disk 10 and zero at infinity. The position variables $\eta$ and $\xi$ are related to cylindrical coordinates by $z = a\xi\eta$ and $r = \alpha[(1+\xi^2)(1-\eta^2)]^{1/2} \cdot \eta = 0$ is off the disk 10 in the plane that includes the disk. $\eta = 1$ indicates the axis of the disk. $\xi = 0$ is on the disk 10 and $\xi = \infty$ is far from the disk 10.

Equation [2] satisfies the boundary conditions at all limits other than on the disk 10 itself: symmetry at the axis, vanishing potential at infinity, and zero flux through the plane of the disk at distances greater than the disk radius. One deduces the coefficients $B_n$ by applying an appropriate boundary condition on the disk. A boundary condition valid for flow adjacent to a solid surface is:

$$i_z = -\nabla_s \cdot \vec{j}_s \quad [3]$$

where $j_s$ is the convected current density in amps per unit of circumference and $i_z$ is normally directed current density evaluated at the disk surface. See, for example, J. Newman, *Electrochemical Systems*, Prentice Hall, New York 1973. Equation [3] says that current leaks out of sheet of convective surface current to the bulk electrolyte. One can show by continuity that:

$$j_{sr} \approx -\epsilon \epsilon_0 \gamma \zeta r \quad [4]$$

where $\gamma = 0.51023\sqrt{\Omega^3/v} \cdot \Omega$ is the rotation rate in radians per second and v is the kinematic viscosity of the liquid. Taking the diffuse layer as thin eliminates consideration of the surface conductivity so there is no second term in this equation. Thus the surface current due to the convection of charge in the diffuse layer is proportional to the radial position and to the rotation rate raised to the 3/2 power.

Inserting [4] into [3], one obtains:

$$i_z = 2\epsilon\epsilon_0 \gamma \zeta \quad [5]$$

The current density flowing from the bulk electrolyte to or away from the surface is a constant over the surface of the disk 10. Using ohm's law and the relationships defined above, one writes:

$$i_z = -\kappa \frac{\partial \phi}{\partial z}\bigg|_{z=0} = \frac{-\kappa}{a\eta} \sum_{n=0}^{\infty} B_n P_{2n}(\eta) M'_{2n}(0) \quad [6]$$

where:

$$M'_{2n}(0) = -\frac{2(2^n n!)^4}{\pi[(2n)!]^2} \quad [7]$$

Equating the results in [5] and [6], one obtains:

$$\sum_{n=0}^{\infty} B_n P_n(\eta) M'_{2n}(0) = \frac{-2\varepsilon\varepsilon_0 \gamma a \zeta \eta}{\kappa} \quad [8]$$

Using orthogonality, one obtains:

$$B_n = \frac{-2\varepsilon\varepsilon_0 \gamma a \zeta}{\kappa} \frac{1}{M'_{2n}(0)} \left[ \frac{\int_0^1 \eta P_{2n}(\eta) d\eta}{\int_0^1 [P_{2n}(\eta)]^2 d\eta} \right] \quad [9]$$

Figure 3:
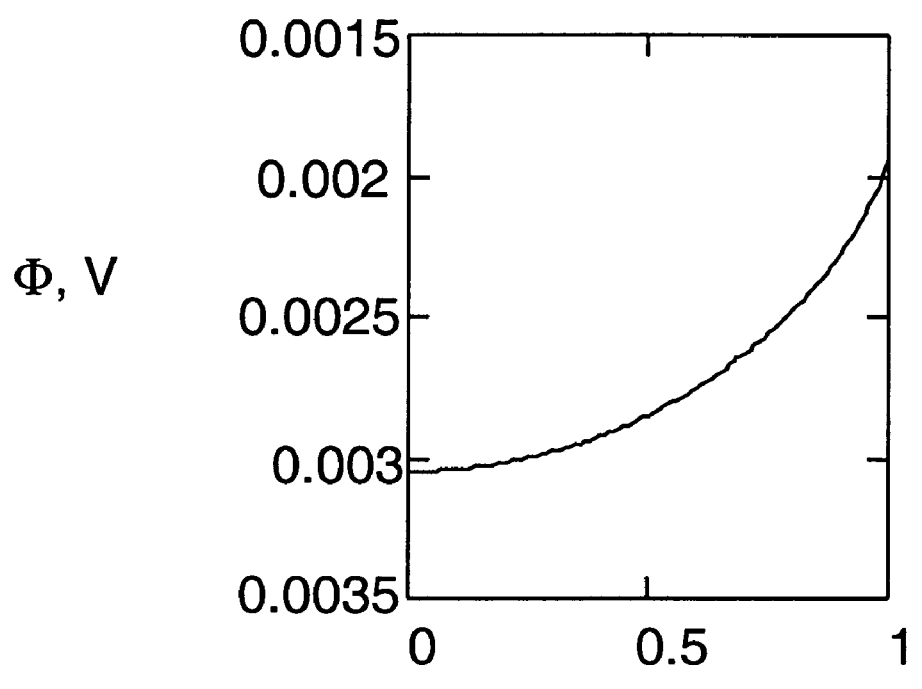
FIG. 3 is a graph of the solution of Equation [2] using coefficients determined using Equation [9]. This solution does not comport with the physical boundary condition that the net current from the disk be zero.

FIG. 3 shows the results of a sample calculation of the expected potential (in V) near the surface of the disk 10. The magnitude of the potential is a maximum at the axis of the disk 10. The calculated potential is a few millivolts. The concentration of electrolyte is 0.1 milliMolar KCl and the zeta potential of the disk is −60 mV. The disk 10 rotates at 2500 rpm. The mobilities of KCl were used to calculate the conductivity.

There is a problem, however, with this result and the formulation of the problem presented. The potential in FIG. 3 is always of the same sign, which means that current is flowing from the disk 10 to infinity where the potential is zero. Physically, one expects the current generated by the rotating disk 10 to close on itself in order to satisfy the condition that no net current flows from the disk 10 (insulating walls, however far away, enclose the domain). For positive charge in the double layer, there must be a net positive current leaving the disk 10 beyond a certain radius and a net negative current flowing to the disk 10 at radii less than this value. Thus, something is missing from the formulation represented by Equations [1]-[9].

Mathematically, a current must flow back from infinity to the disk 10 in order to satisfy the requirement of zero net current flow from the disk 10. The opposing current must equal the integrated convective current departing from the disk, given as Equation [5] multiplied by the area of the disk. Thus the total current flowing from the disk 10 becomes zero as required.

The dimensionless current distribution that returns current from infinity to the disk is given by (see Sides and Hoggard, Langmuir 2004, 20, 11493-11498 for derivation of this result.):

$$i^*(r^*) = \frac{1}{2} \frac{1}{\sqrt{1-(r^*)^2}} \quad [10]$$

where r* is dimensionless radius r/α. Thus the new current distribution that forms the boundary condition at the electrode, replacing Equation [5], is:

$$i_z = 2\varepsilon\varepsilon_0 \gamma \zeta \left(1 - \frac{1}{2} \frac{1}{\sqrt{1-(r^*)^2}}\right) \quad [11]$$

Integration of this current distribution over the disk yields a zero net current flowing from the disk 10. Use of this current distribution means that the coefficients $B_n$ are correctly calculated according to the following equation, where Equation [11] has been converted to rotational elliptical coordinates:

$$B_n = \frac{-2\varepsilon\varepsilon_0 \gamma a \zeta}{\kappa} \frac{1}{M'_{2n}(0)} \left[ \frac{\int_0^1 \left(\eta - \frac{1}{2}\right) P_{2n}(\eta) d\eta}{\int_0^1 [P_{2n}(\eta)]^2 d\eta} \right] \quad [12]$$

Figure 4:
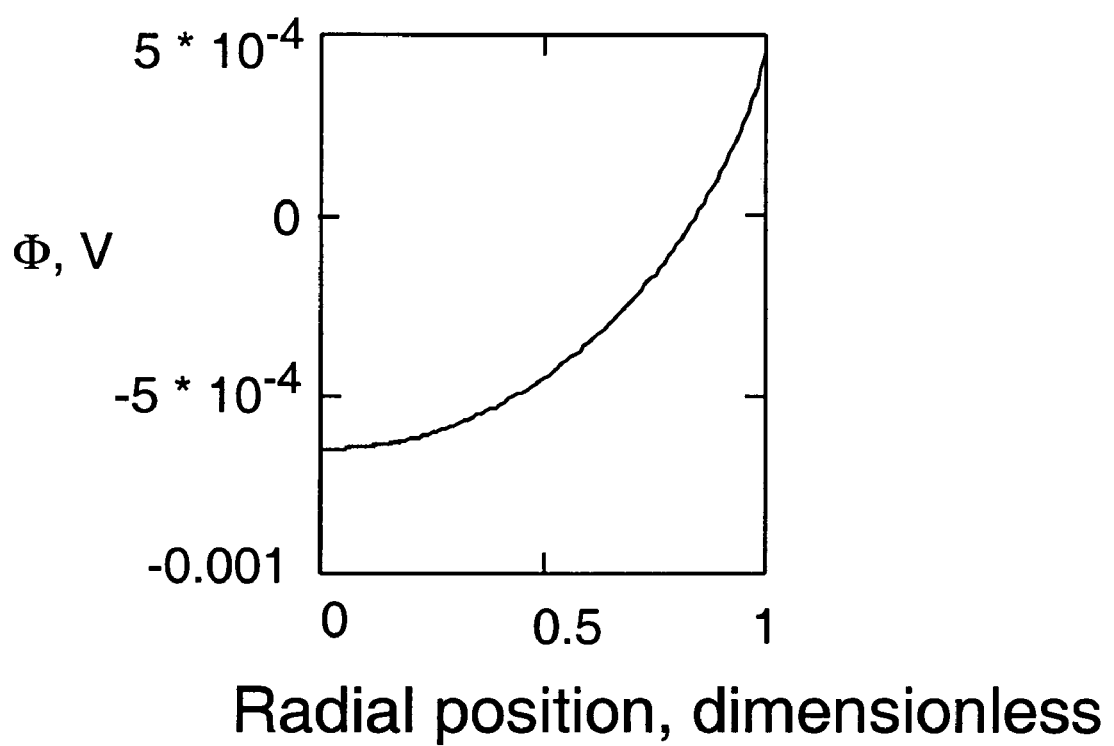
FIG. 4 is a graph of the solution of Equation [2] using coefficients determined using Equation [12]. This solution results from the boundary condition that the net current from the disk be zero and is the physically meaningful solution.

FIG. 4 shows the results of the calculation of the potential at the surface of the disk 10 according to Equation [2] when the coefficients obey Equation [12]. The potential now crosses zero so that current flows in solution from the outer region of the disk 10 to the inner region, as one expects on physical grounds. In essence, all potentials of FIG. 3 have been shifted upward by an amount required to drive the opposing current, so that the net current from the disk 10 is zero. There is a circle of zero potential on the disk 10 that is connected by a surface of rotation at zero potential extending to infinity.

At a concentration of 0.1 milliMolar potassium chloride in water at 25 degrees centigrade with a zeta potential of −60 mV on a 2 inch diameter disk rotating at 2500 rpm, we expect to measure a potential of −657 μV between electrodes 16 and 18 placed on the axis immediately adjacent to the disk and far from the disk, respectively. The prediction is that the measured potential should depend on the rotation rate to the 3/2 power and should be inversely proportional to the concentration.

Experimental Measurement of Streaming Potential with a Rotating Disk

In this section we describe experimental measurement of the streaming potential. Using these results, we have verified the theory of the previous section by experimentation, succeeding where prior attempts to observe the 3/2 power dependence on the rotation rate failed. The following is a description of the set-up and measurements made according to the present invention that successfully verifies the theory described in the previous section.

Working and Counter Electrode Preparation.

In preparing the working and counter electrodes, pure silver starting materials are generally desired to reduce measurement error in the working electrode 16 and counter electrode 18. In the experiments discussed below, the electrodes 16, 18 are 99.99% pure and formed with twelve gauge silver wire coated with polyolefin heat shrink tubing. Approximately 1 mm of the wire was exposed and treated according to a recipe combining the methods of Ives and Janz and Westermann-Clark (D. J. Ives and G. J. Janz, *Counter Electrodes: Theory and Practice*, Academic Press: New York, 1961; and A. Braem, Ph. D., Thesis, Carnegie Mellon University, 2001). Two coated wires were soaked for one hour in a concentrated ammonia solution. They were then washed with deionized water, dipped in concentrated nitric acid to roughen the surface, and placed in a 0.1 Molar HCl solution. A 0.1 mA current was passed for one hour by a current source through two silver wires connected in parallel at the positive terminal to a nitric acid cleaned copper wire at the negative terminal. This resulted in a plum colored AgCl coating. The electrodes 16, 18 were then rinsed and soaked in de-ionized water for twenty-four hours before being tested on the electrometer. Satisfactory electrode potential differences fluctuated less than 0.1 mV and ideally had an open circuit potential difference less than 1.0 mV.

Disk Materials.

Disks 10 having a diameter of 50 mm were used in all experiments discussed with reference to FIGS. 5-12. In the streaming potential experiments, a silicon wafer was cleaned by soaking 20 minutes in Chromerge and five minutes in deionized water. This wafer is called the "cleaned" silicon wafer. Other silicon wafers tested in streaming current measurements were only rinsed in deionized water after being taken from the packaging; these are called "rinsed" wafers. Also used were an indium tin oxide coated glass disk washed in ethanol followed by a deionized water rinse and a sapphire disk soaked 20 minutes in Chromerge followed by a deionized water rinse.

The specific criteria and specifications for the experiments and embodiments of the present invention, as provided both above and below, are to assist the reader in evaluating the results of the experiments. Some or all of the criteria and specifications may be changed without departing from the spirit and scope of the present invention. For example, working and counter electrodes made of other materials could be used by one skilled in the art.

Initial Unsuccessful Measurements at the Edge of the Disk.

We initially made measurements with an apparatus in which we placed a working electrode 16 at the edge of a monolithic test disk 10 (position 4 in FIG. 1) and measured the potential relative to a counter electrode 18 located far from the disk 10 (position 0 in FIG. 1). We obtained erratic results with a sublinear exponent on rotation rate. Referring back to the theory illustrated in FIG. 4, one can see that the edge of the disk 10 is where the measured potential is most sensitive to position. Indeed, the potential crosses zero not far from the edge. Thus placing a working electrode 18 at the edge of the disk 10 will tend to produce inconsistent results.

Successful Measurement of the Streaming Potential's Dependence on the Rotation Rate Our insight, guided by the theory, is that superior results can be obtained by placing the working electrode on the axis near the surface (position 1 in FIG. 1) with a counter electrode 18 far from the disk. (position 0 in FIG. 1). In one embodiment, the working electrode 16 may be near but not in contact with the surface. In this embodiment, the working electrode 16 may be stationary while the disk 10 rotates. In another embodiment, the working electrode 16 may be integral with the disk 10 at or near the axis of rotation. In this embodiment, the working electrode 16 moves with the disk 10.

Figure 5:
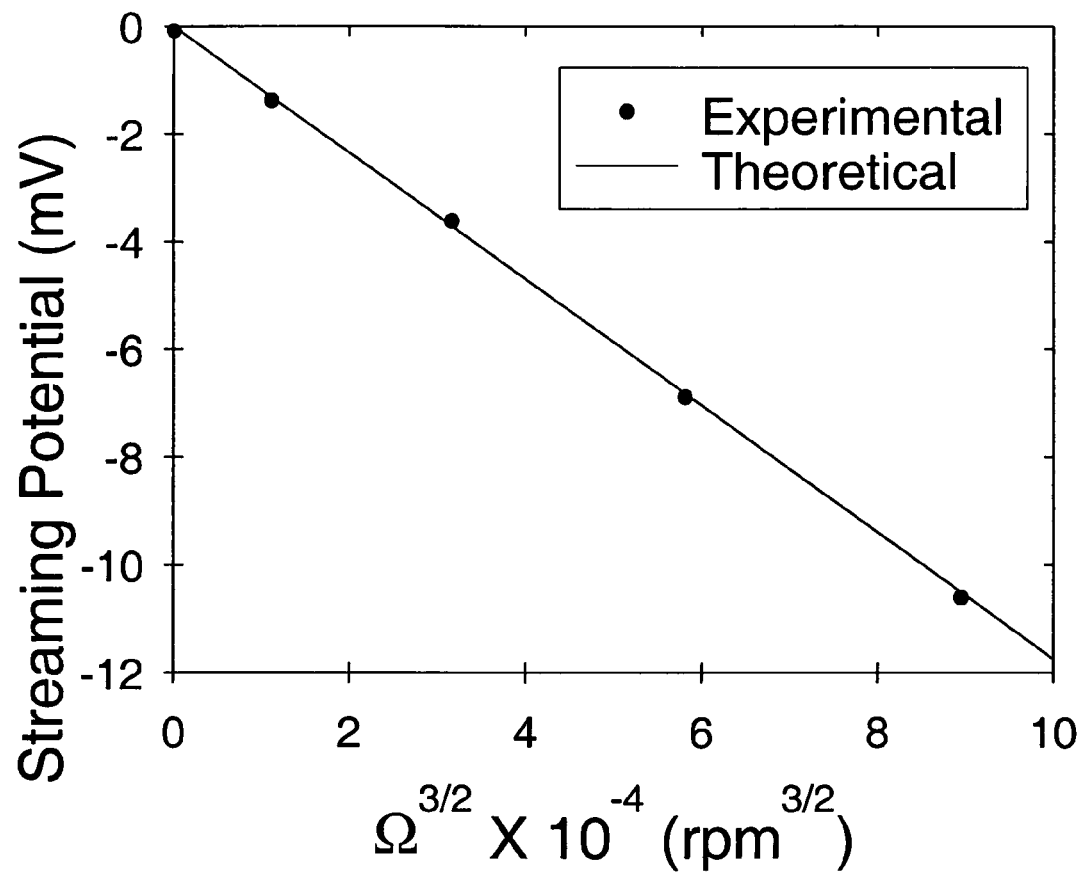
FIG. 5 is a chart illustrating theoretical and experimental streaming potential as a function of rotation rate raised to the 3/2 power on a silicon wafer.

The measured data was obtained under the following conditions. The disk 10 was 50 mm diameter silicon oxide, and the electrolyte was $10^{-5}$ Molar KCl. The working electrode 16 was placed outside the double layer at the axis and the counter electrode 18 was placed approximately 20 cm from the disk 10. If one makes measurements of potential difference based on this positioning and compares it to the theory, with both measurement and theory plotted as a function of rotation rate of the disk 10, one obtains the results shown in FIG. 5 where the data points represent the measured streaming potential plotted against the 3/2 power of the rotation rate of the spindle/surface assembly of FIG. 2. FIG. 5 shows the clear dependence of the measured streaming potential on the 3/2 power of the rotation rate.

Use of the Theory for Conversion of the Streaming Potential to Zeta Potential

The only unknown in the theory, specifically Equations [2] and [12], is the zeta potential. We convert the streaming potential data into zeta potential by choosing the zeta potential to get the best agreement with the theory. The result of using only the zeta potential to fit the theory of Equations [2] and [12] to the data of FIG. 5 appears in FIG. 6. The agreement in curvature between the theory and the data shows the 3/2 power predicted in Equation [4] (see the quantity y in this equation).

Figure 6:
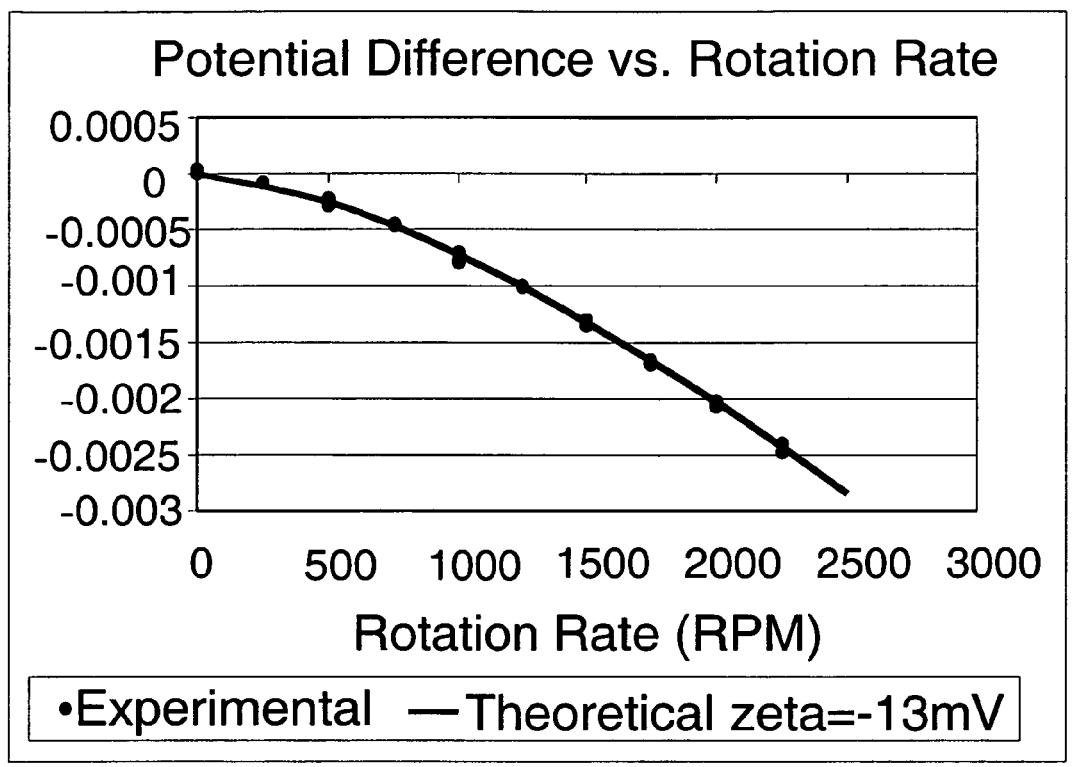
FIG. 6 is a chart showing both the predicted streaming potential at various rotation rates of the disk and experimentally measured values. The zeta potential, the only unknown in the theory, is used to fit the experimental data to the theory. Note both the close overlap of the experimentally measured values with the theoretically predicted values and the dependence of the zeta potential on the rotational rate raised to the 3/2 power.
Figure 7:
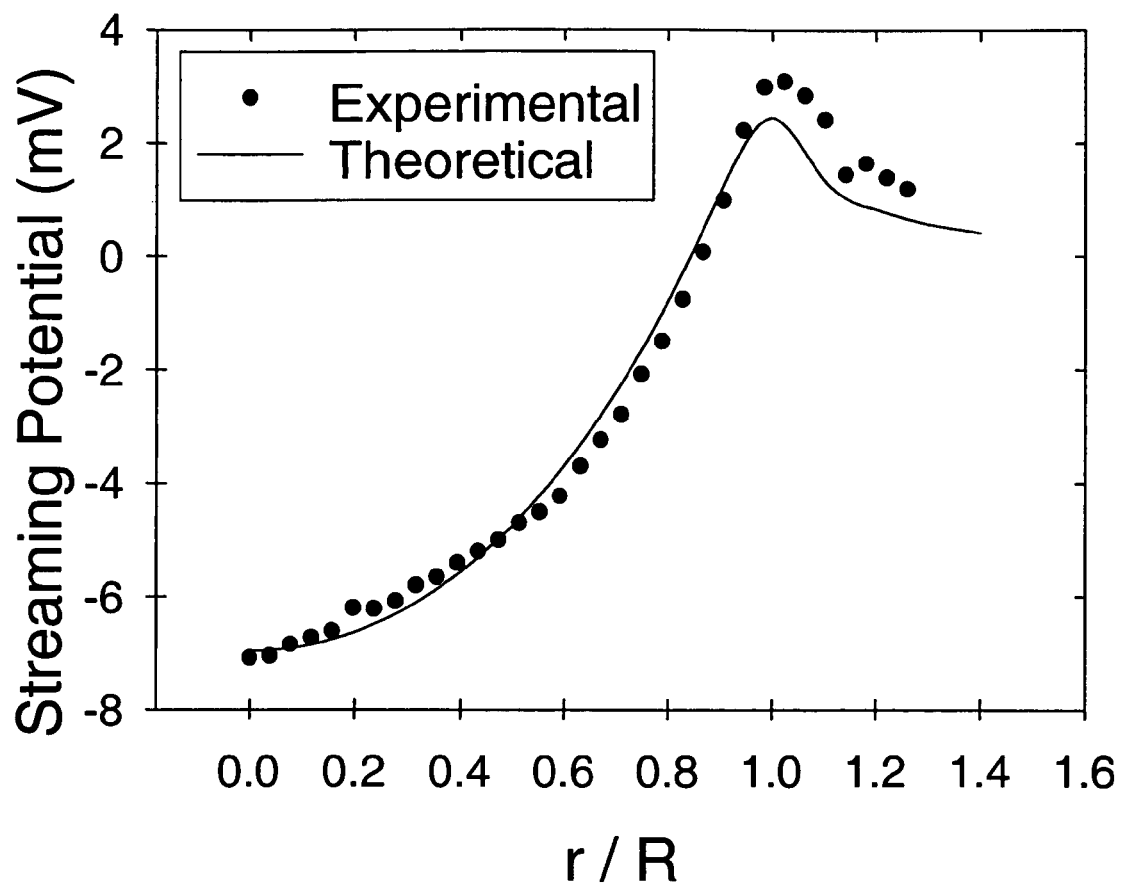
FIG. 7 is a chart illustrating theoretical and experimental streaming potential as a function of radial position on a silicon wafer.
Figure 8:
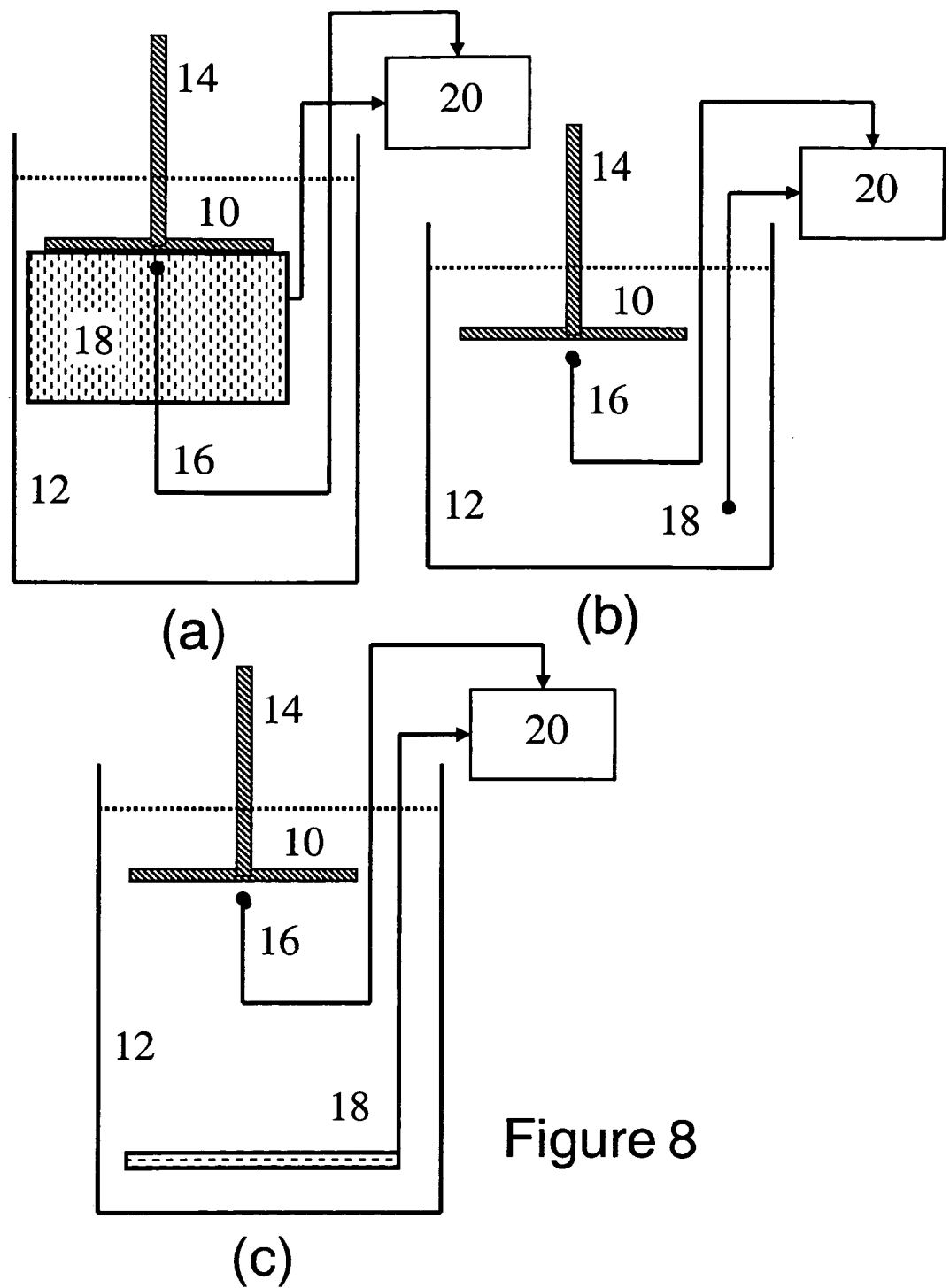
FIGS. 8a-8c are schematics illustrating several embodiments of streaming current measurement apparatuses.
Figure 9:
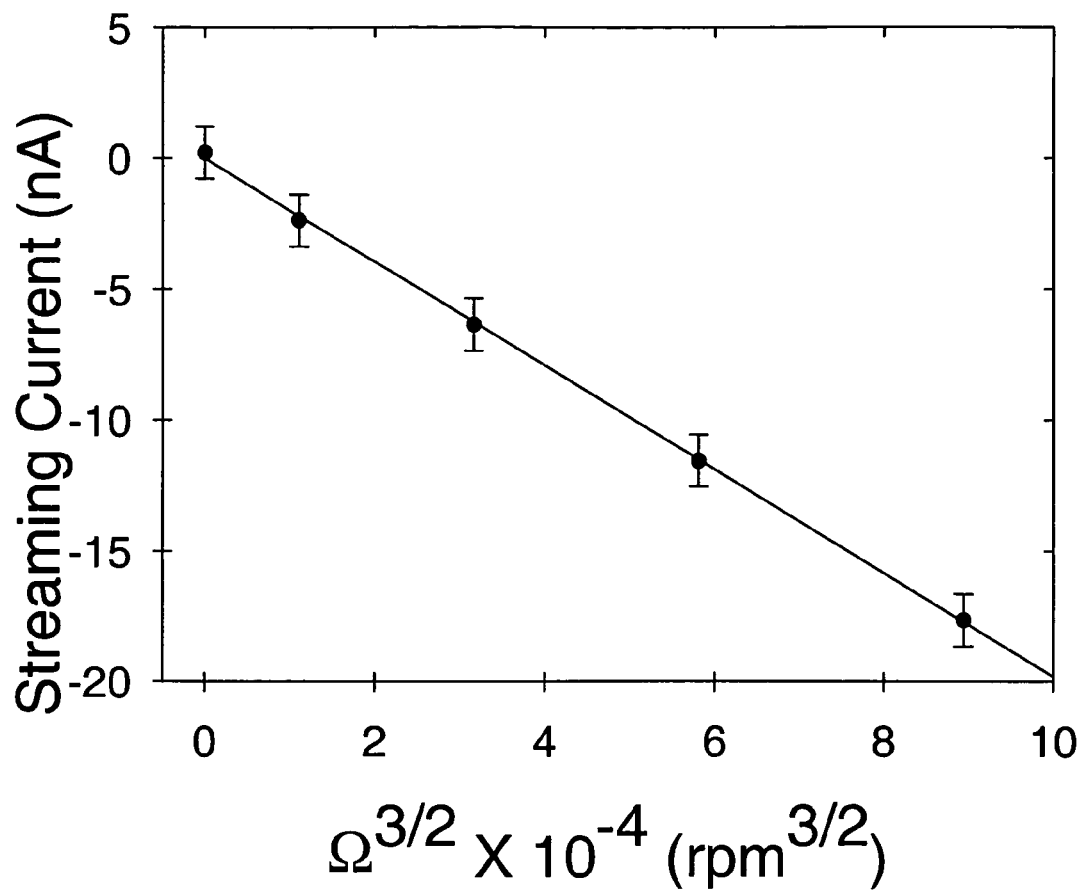
FIG. 9 is a chart illustrating experimentally measured streaming current as a function of rotation rate raised to the 3/2 power.

FIG. 7 shows an experimental comparison to the calculation of FIG. 4 in order to demonstrate that the zeta potential deduced from the theory and FIG. 6 could be used to predict measurements elsewhere on the disk. We scanned the working electrode 16 (initially at position 1 in FIG. 1) radially across the disk 10 and measured streaming potential as a function of position along the disk 10. Using the zeta potential found according to the method describe above and the theory embodied in Equations [2] and [12] we calculated the expected radially dependent streaming potential profile; the experimentally measured profile agrees well with the theoretical line so produced near the axis and beyond, with no additional fitting of the data to the theory. Note the crossing of zero potential in both the theory and the data as shown in the sample calculation of FIG. 4. Measured potentials are largest when the working electrode 16 is on or near the axis relative to the counter electrode 18 placed as far from the disk as the vessel 12 permits. Measuring the potential at the disk 10 edge can give results that are difficult to interpret.

It has been found that placing the working electrode 16 at the axis of rotation of disk 10 is advantageous because the best signal is obtained at the axis where the radial velocity of the fluid is zero.

Implementing the Invention

There is some latitude in the physical configuration of required elements of the technology (e.g, the disk 10 and electrodes 16, 18) and there are practical difficulties in positioning some of these elements in accordance with the theory set forth above (e.g, one cannot truly position the counter electrode 18 at an infinite distance from the disk 10). The following sections describe several practical embodiments of the present invention, although other embodiments may also be used with the present invention.

The electrodes 16, 18 may be, but are not limited to commercially available silver/silver chloride electrodes or calomel electrodes. The electrodes 16, 18 may also be created by one skilled in the art. The tests described herein were performed using silver/silver chloride electrodes made in our laboratories. Several embodiments of the electrodes 16, 18 are discussed herein, although other embodiments of the electrodes may also be used.

Guidelines for the Working Electrode.

It is generally preferred that the working electrode 16 does not contact the disk 10. In particular, it is often advantageous for the minimum separation between the working electrode 16 and the disk 10 to be at least ten times the Debye length, a commonly known characteristic length of electrolyte solutions. However, greater or lesser distances may also be used up to but not including contact with the disk. The Debye length $\lambda$ characterizes the scale of the region near solid surfaces where significant space charge is present and is calculable for any solution by the well known equation, $$\lambda = \left(\frac{\varepsilon RT}{F^2 \sum_i z_i^2 c_{i\infty}}\right)^{1/2}. \quad [13]$$

Here $\varepsilon$ is the solution permittivity, R is the gas law constant, T is temperature, F is faraday's constant, $z_i$ is the charge on ionic species i, and $c_{i\infty}$ is the concentration of that ionic species far from the disk. The Debye length depends on the inverse square root of ionic strength of the solution. If the working electrode 16 is positioned inside ten Debye lengths from the surface, the electric potential measured will not be solely characteristic of the desired quantity. The Debye length is not often greater than one µm for solutions where a measurement can be made, so this limitation is not severe. The technology disclosed herein should therefore be applicable to at least all working electrode 16 positions greater than ten Debye lengths away from the disk 10 with the maximum separation subject to constraints described in the next paragraph, although more closely-spaced working electrodes 16 may be used with the present invention, particularly as new technologies evolve.

The principle governing the maximum separation of the working electrode 16 from the disk 10 is that the value of the electric potential decreases as the working electrode 16 moves away from the disk 10. Thus the practical maximum separation is set by the ability to make a meaningful measurement of potential with respect to the counter electrode 18. In one embodiment, the maximum gap between the working electrode 16 and the disk 10 is 5% of the disk radius, which is a compromise between the principle of measuring the largest voltage and ease of positioning the working electrode 16. However, greater and lesser distances may be used with the present invention.

As mentioned above, it is often desirable for the working electrode 16 to be located as close as possible to the disk's axis of rotation. While the optimal lateral position for the working electrode 16 is the axis, one can still make a measurement characteristic of zeta away from the axis. In one embodiment, measurements may be made out to one half the disk 10 radius from the axis. Measurements may be made at other locations, but the measured potential generally decreases as the working electrode 16 moves away from the axis, thereby leading to decreased accuracy as one moves further from the axis of rotation and closer to the edge of the disk 10. For example, in another embodiment, the measurements are made up to one radius from the axis of rotation (e.g., at the edge of the disk).

The size of the working electrode 16 will be specified in terms of its lateral dimension. As a general rule, smaller working electrodes 16 are better. The effective maximum size is less easy to define. A large working electrode 16 is usually not preferred because it would interfere with the recirculating flow of current in solution and because its sensing tip averages the potential over its dimension. Thus, in some embodiments, the working electrode 16 is made as small as practical. In other embodiments, the working electrode 16 is not larger than one half of the disk 10 radius. However, other working electrode 16 sizes may also be used.

In the embodiment used to generate the data discussed above, the working electrode 16 was 2 mm in diameter, the disk 10 radius was 25 mm, and the gap between the working electrode 16 and the disk 10 was 1 mm. The lateral position of the working electrode 16 was on the disk's axis of rotation.

Guidelines for the Counter Electrode.

The location of the counter electrode 18 is more flexible than that of the working electrode 16. In general, the farther away from the disk 10 one can locate the counter electrode 18, the better. The electric potential is distributed in a continuous fashion in the electrolyte surrounding the disk 10. The maximum magnitude is at the axis very near the disk 10. An electric potential value of zero can be found on an axisymmetric imaginary surface extending from a position near the edge of the disk 10 out away from the disk 10. The value of the electric potential decays from its maximum near the disk 10 at the axis to zero as one approaches this surface. The farther from the position of the maximum potential, the larger the measured voltage. It has been found that a good compromise choice for the counter electrode 18 is three and one half radii from the center of the disk 10, because that position gives a substantial signal without making the vessel too large. Other distances for the counter electrode 18 may also be used. In the embodiment used to generate the data with reference to FIGS. 1-7, the counter electrode 18 was 20 cm from the disk.

Since the electric potential is not a strong function of position far from the disk 10, the size of the counter electrode 18 may have greater variability than that of the working electrode 16. A practical maximum would be that the lateral dimension of the counter electrode 18 need not exceed the diameter of the disk 10, although larger counter electrodes 18 may also be used.

Use of Streaming Current to Measure the Zeta Potential

Theory of the Relationship Between Streaming Current and the Zeta Potential.

Another embodiment of the present invention includes apparatuses and methods for measuring streaming current. One measures a streaming current by offering the convected current an electronic auxiliary path through an ammeter 20 to close the "circuit"; this is accomplished with near perfect collection efficiency in a thin-gap apparatus because the ohmic resistance of the flow channel is typically high relative to the resistance for flow through the auxiliary circuit. In the rotating disk 10 configuration, however, the working electrode 16 and the counter electrode 18 do not capture all of the convected current produced by the rotation. As a result, the present invention introduces the concept of "current collection efficiency" when using a rotated surface 10 in a streaming current measurement.

FIGS. 8a-8c illustrate several embodiments for measuring streaming current. In each embodiment, the counter electrode 18 is away from the disk 10 and the working electrode 16 is close to the disk 10 at the axis of rotation. Some fraction of the total streaming current flowing from the disk 10 travels through the current collection system, including the ammeter 20. Theory shows that a uniform current density flows from the surface of the disk 10 when it is rotated, as shown in Equation [5]

Most of this current returns to the disk 10 surface without passing through the ammeter 20 that connects electrodes 16, 18 positioned as shown in FIGS. 8a-8c. A current collection efficiency can be defined as:

$$\mathit{Eff} = I_{meas}/(i_z \pi a^2) \quad [26]$$

where $I_{meas}$ is the measured current. When Eff is known, zeta can be calculated via Equations 5 and 26. If Eff does not vary with conductivity and the magnitude of zeta, Eff only depends on the geometry of the system.

Experimental Measurement of Streaming Current with a Rotating Disk

FIGS. 8a-8c illustrates three embodiments of a streaming current measurement apparatus. These embodiments will be described with reference to experiments related to the present invention. In the embodiment illustrated in FIG. 8a-8c, a 50 mm disk surface 10 is attached to a spindle 14, immersed in electrolyte held by a container 12, and rotated at arbitrary rates between zero and 2500 rpm. These and similar embodiments may also be used for measuring streaming potential. The embodiments in FIGS. 8a-8c will be described with reference to several experiments related to the present invention. In the embodiments of FIGS. 8a-8c, a Ag/AgCl working electrode 16 is placed on the axis of the disk near the disk 10 surface and attached to the positive terminal of the meter 20 operating in current mode. With regard to the counter electrodes 18, FIGS. 8a-8c illustrate three different embodiments, although other embodiments are also possible. For example, the configuration of FIG. 8c may be used for both streaming potential and streaming current measurements, and different electrode shapes, materials, and locations may be used for measurement of either or both streaming potential and streaming current. The size of the beaker was two liters for FIGS. 8a and 8b, and was 400 mL for FIG. 8c. In each experiment, the 3/2 power dependence on rotation rate was observed as described herein.

In FIG. 8a, a 2.5 inch diameter Ag/AgCl cylindrically shaped counter electrode 18 in the form of a "skirt" is attached to the negative lead of the meter 20. The top of this counter electrode 18 is at the same height as the disk surface 10. Both the top and bottom of the skirt are open on the counter electrode 18. In FIG. 8b, the counter electrode 18 is a wire tip placed far from the disk 10, similar to that for streaming potential measurement. In FIG. 8c, the counter electrode 18 is a flat plate placed in the bottom of the container 12.

The specific criteria and specifications for the experiments and embodiments of the present invention, as provided both above and below, are to assist the reader in evaluating the results of the experiments. Some or all of the criteria and specifications may be changed without departing from the spirit and scope of the present invention.

Streaming Current Measurements

Using the experimental setup in FIG. 8a, we measured the streaming current near the surface of a rinsed silicon wafer 10 as a function of rotation rate in a $10^{-6}$ M KCl solution. A working electrode 16 was placed on the axis of the disk 10 near the disk surface and a "skirt" shaped counter electrode 18 around the outside of the disk 10 (FIG. 8a). The surface was a de-ionized water washed silicon wafer in a $10^{-6}$ M KCl solution. The rotation rate was varied from 0 to 2000 rpm. The measured streaming current as a function of rotation rate raised to the 3/2 power from one experiment appears in FIG. 9. The solid circles are experimental measurements and the line is a linear fit to the slope of the data. The error bars result from fluctuations in the current due to measurement of an unfiltered signal.

As with the streaming potential measurements, the collected streaming current was proportional to the 3/2 power of the rotation rate in accordance with Equation [5]. The measured current was of order 10 nA, but the total current $\pi a^2 i_z$ calculated from Equation [5] was of microamp order.

Conversion of Streaming Current Measurements to Zeta Potential

Because only a fraction of the total streaming current is collected, Equation [5] cannot be used to calculate the zeta potential. Instead, a current collection efficiency was defined (Equation [26]) and its values for the three variants of counter electrodes 18 shown in FIG. 8a-8c were determined experimentally.

In order to determine the current collection efficiency, both streaming potential and streaming current measurements were used. Silicon wafers 10, an indium-tin-oxide coated glass disk and a sapphire disk, were tested to calculate the current collection efficiency over a range of zeta potentials. The streaming current measurements were made in the same solution as the streaming potential measurement. We first measured the streaming potential of a disk 10 in $10^{-5}$ M KCl to determine $\zeta$. The streaming current was then measured as a function of rotation rate in the same solution and the efficiency was calculated from Equations [5] and [26]. If the current collection efficiency determined in the described manner is robust, it should depend neither on the value of the zeta potential nor on the concentration of the electrolyte.

Figure 10:
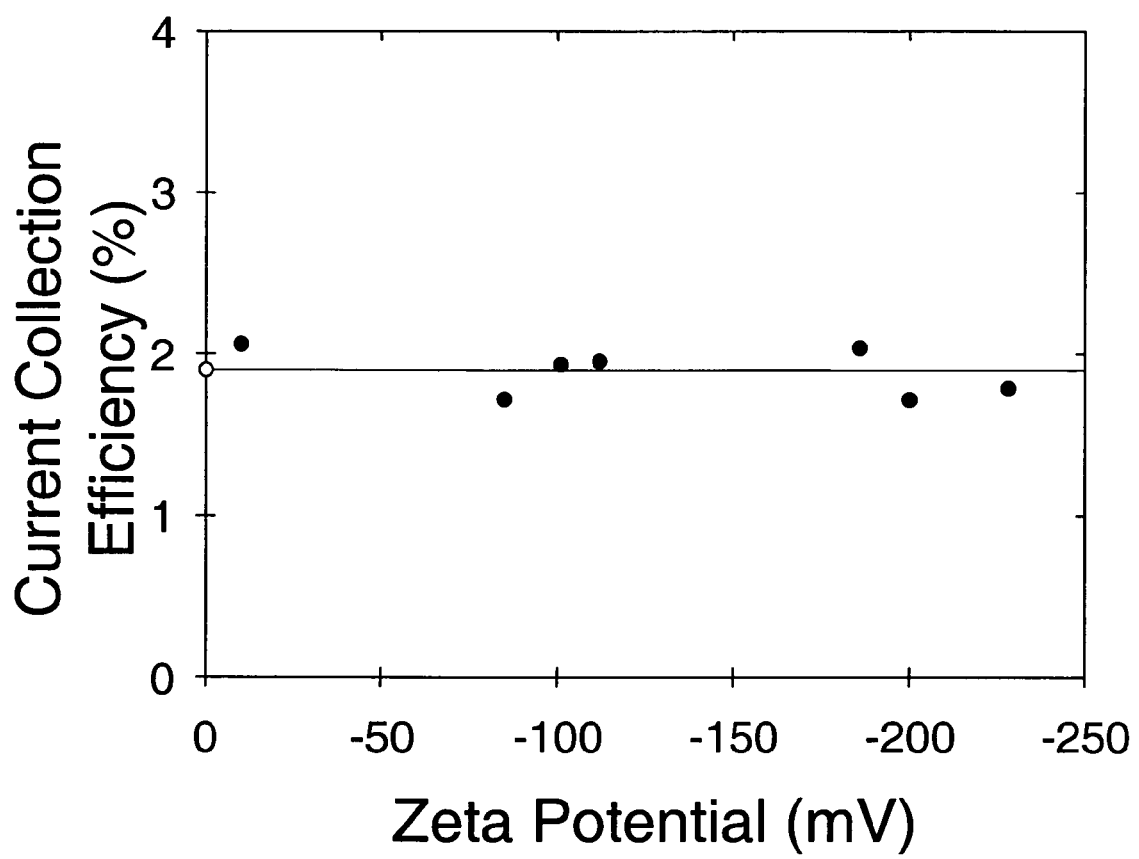
FIG. 10 is a chart illustrating current collection efficiency as a function of zeta potential.
Figure 11:
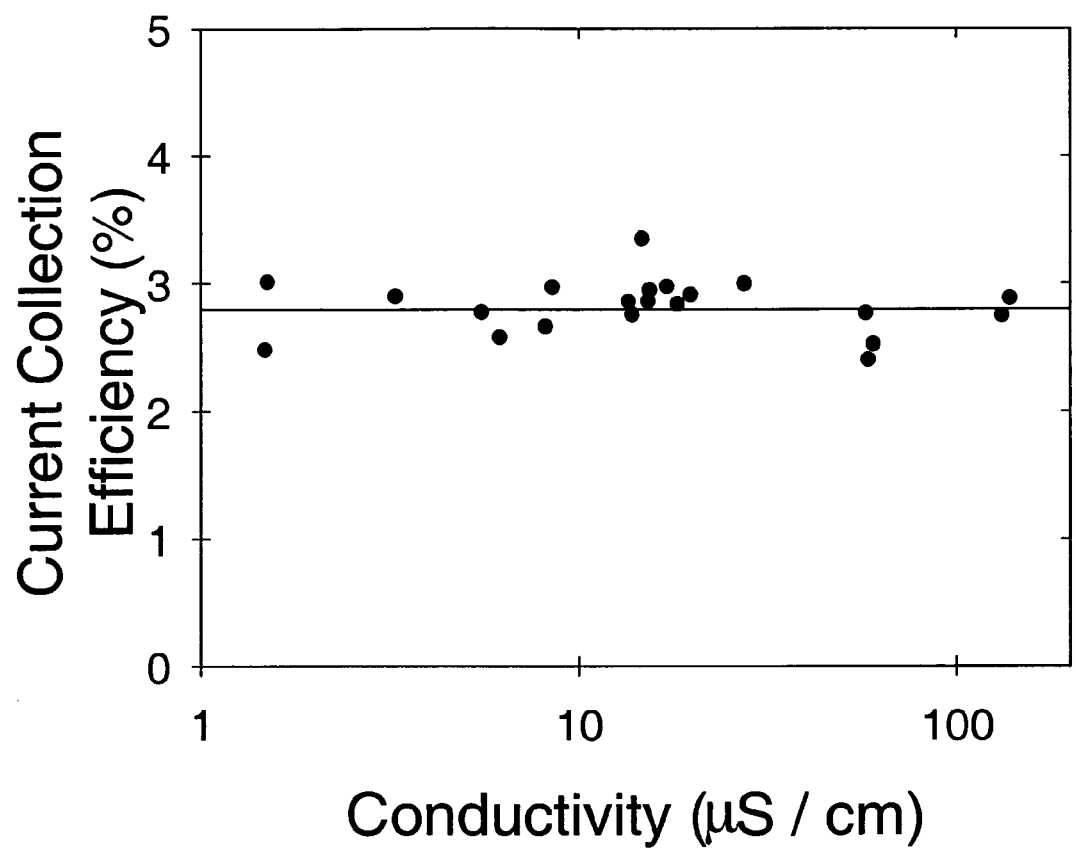
FIG. 11 is a chart illustrating current collection efficiency as a function of solution conductivity.

First, using the apparatus shown in FIG. 8a, the current collection efficiencies were determined for disks 10 with varying zeta potentials. The disks 10 tested were silicon, indium tin oxide, and sapphire. The calculated Eff was plotted in FIG. 10 against the zeta potential as described above. The line corresponds to a collection efficiency of 1.9%. The results appearing in FIG. 10 show that the current collection efficiency was independent of the magnitude of zeta from 0 to −250 mV. We also determined the collection efficiency of the apparatus in FIG. 8c for solutions of various KCl concentrations. The results appearing in FIG. 11 show that the collection efficiency was independent of concentration in the range of concentrations shown. The solid line corresponds to Eff=2.8%. This figure shows Eff to be constant over the range of conductivities that can be measured using streaming current and streaming potential measurements. Using this efficiency, the zeta potential can be calculated at higher solution conductivities using streaming current measurements. Thus the collection efficiency defined by Equations [5] and [26] accurately converts streaming current measurements to zeta potential.

The current collection efficiency was measured for each apparatus depicted in FIGS. 8a-8c. The value depends on the placement and shape of the counter electrode 18. For the setups shown in FIGS. 8a, 8b, and 8c, the current collection efficiencies were 1.9±0.1%, 0.76±0.1%, and 2.8±0.2%, respectively. The streaming current of a rotating disk 10 can thus be used to determine the zeta potential within approximately 10% of its value.

Figure 12:
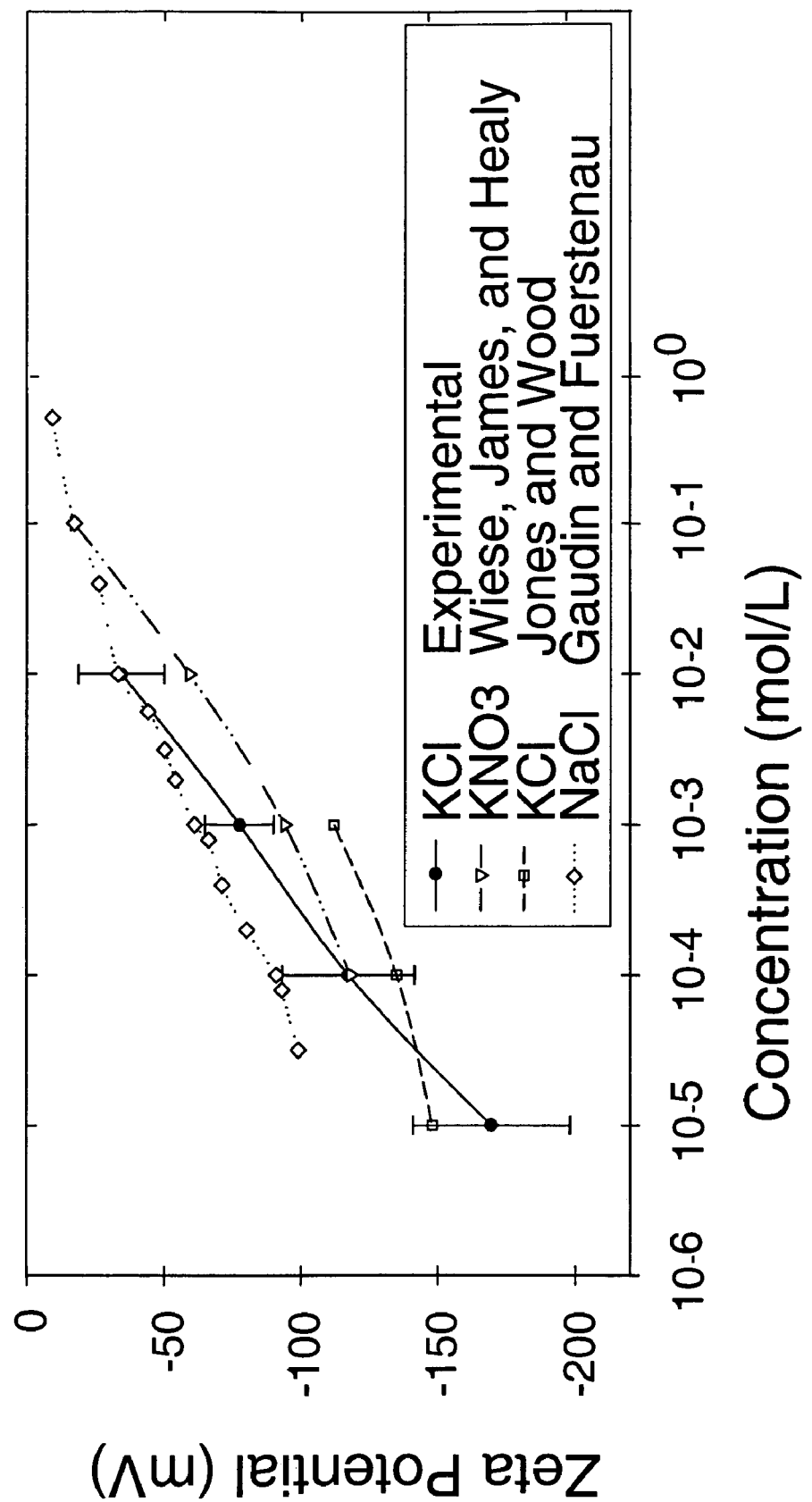
FIG. 12 is a chart illustrating zeta potential of silicon dioxide as a function of aqueous salt concentration.

FIG. 12 illustrates the zeta potential of silicon dioxide as a function of aqueous salt concentration. The solid circles with error bars are zeta potentials calculated from streaming current measurements on three deionized water rinsed silicon wafers in KCl concentrations from rotated from $10^{-6}$ to $10^{-2}$ M and Equations [5] and [26], and 0 to 2500 rpm using the experimental setup shown in FIG. 8a with Eff=1.9%. This data is compared to other zeta potential measurements made in various salt solutions at neutral pH, using streaming potential measurements in capillaries, and found in the literature: the open squares are results of Jones and Wood (Jones, G; Wood, L; *Journal of Chemical Physics,* 1945, 13, 106-121) in KCl solutions using streaming potential measurements across a cylindrical, vitreous silica capillary; the open triangles are the results of Wiese et al.(Wiese, G. R.; James, R. O.; Healy, T. W.; *Disc. Faraday Soc.,* 1971, 52, 302-311; Healy, T. W.; White, L. R. *Adv. Colloid Interface Sci.,* 1978, 9, 303) in $KNO_3$ solutions using the same technique as Jones and Wood; and the open diamonds are data of Gaudin and Fuerstenau (Gaudin, A. M.; Fuerstenau, D. W.; *Trans. AIME* 1955, 202, 66-72; Hunter, R. J.; Wright, H. J. L.; *J. Colloid* and *Interface Sci.,* 1971, 37, 564-580) in NaCl solutions using streaming potential measurements across a porous plug of silica. The plot shows agreement of streaming current measurements using current collection efficiencies to determine zeta potentials in a rotating disk 10.

Conclusion

The foregoing description has focused on steady state measurements of streaming current and streaming potential on disk-shaped surfaces to allow calculation of the zeta potential from electrical measurements. Other measurement protocols are envisioned and encompassed by this invention. For example, an operator skilled in the art could program the rotator to follow a time dependent function so that the expected streaming potential or streaming current would rise and fall sinusoidally with a frequency specified by the operator. The operator could then apply methods of signal detection such as Fast Fourier Transforms of discrete data to improve the signal to noise ratio of the measurement. The applied rotation function could also be a sawtooth pattern or a square wave pattern.

Streaming potential measurements can be made in low conductivity solutions using a rotating disk 10. Improved results are generally obtained when the working electrode 16 is placed on the axis of rotation of the disk 10 and when the gap between the working electrode 16 and the disk 10 is small and known because the streaming potential measurement depends strongly on this gap. Streaming potential measurements can be used to calculate the zeta potential of any disk-shaped surface because of the complete theory relating the two, but practicalities of measurement using present technology generally limit the concentration of test solutions to approximately 10 milliMolar and below.

Streaming current measurements on a rotating disk 10, which should not be subject to the same constraint on concentration, cannot be directly related to the zeta potential by theory because only a fraction of the total current flows through the ammeter 20. Nevertheless a current collection efficiency that depends on the particular geometry of the apparatus in use can be deduced. The current collection efficiency was shown to be independent of zeta potential and solution conductivity. Streaming current measurements might be possible in solutions of higher conductivity than are possible with streaming potential measurements using the same disk 10.

Although the present invention has been described in terms of specific embodiments and experiments, the present invention is applicable to many modifications and variations. The examples provided herein are illustrative and not limiting, and those and other variations are possible with the present invention. For example, the particular set-up and measurement parameters, rotational speeds, flow regimes (laminar or turbulent) electrolyte solution, and other criteria, as well as the composition, purity, shape, position, and size of the electrodes 16, 18 and other devices and components may vary from that described herein. Furthermore, the present invention has been described in terms of a working electrode and a counter electrode, although more than two electrodes may be used with the present invention. For example, more than one working electrode and/or more than one counter electrode may be used. Furthermore, although the present invention has been generally described in terms of rotating disks 10, advantages of the present invention can also be realized, for example, with disks which are moved in an oscillating, back and forth motion and with solids of regular or irregular shapes. These and other variations and modifications are within the spirit and scope of the present invention, are it is intended that the foregoing specification and the following claims cover such modifications and variations.

The invention claimed is:

1. An apparatus for measuring a streaming potential or streaming current corresponding to a rotating surface, wherein the surface has a radius and wherein the surface rotates around an axis of rotation, comprising:
   a working electrode located within one radius from the axis of rotation and within three radii from the surface, and wherein the working electrode does not contact the surface;
   a counter electrode, wherein the counter electrode is cylindrical in shape, has a radius greater than that of the surface, and wherein the surface is located within the counter electrode;
   a meter connected to the working electrode and the counter electrode;
   a rotatable spindle on which the surface is mounted; and
   a container for holding electrolyte, wherein the working electrode, counter electrode, and surface are located within the container.

2. The apparatus of claim 1, wherein the working electrode is located on the axis of rotation.

3. The apparatus of claim 1, wherein the working electrode is located at least ten Debye lengths from the surface.

4. The apparatus of claim 1, wherein the working electrode is within 5% of the radius from the surface.

5. The apparatus of claim 1, wherein the meter measures electrical current passing through the electrodes and the meter.

6. The apparatus of claim 1, wherein the meter measures electrical voltage at the working electrode relative to the counter electrode.

7. The apparatus of claim 1, wherein the surface is not a disk centered on the axis of rotation, and wherein the radius includes at least two different radial distances between the axis of rotation and at least two edges of the surface.

8. A method for measuring a streaming potential or streaming current corresponding to a rotating surface, wherein the surface has a radius, comprising:
   rotating the surface around an axis of rotation; and
   measuring the streaming potential or streaming current at a location within one radius from the axis of rotation and within three radii from the surface, wherein the location does not contact the surface.

9. The method of claim 8, wherein measuring the streaming potential or streaming current includes measuring the streaming potential or streaming current relative to a location which does not rotate with the surface.

10. The method of claim 8, wherein measuring a streaming potential or streaming current includes measuring streaming potential.

11. The method of claim 8, wherein measuring a streaming potential or streaming current includes measuring streaming current.

12. The method of claim 8, wherein rotating includes rotating the disk in one direction around the axis of rotation.

13. The method of claim 8, wherein rotating includes oscillating the surface in different directions around the axis of rotation.

14. The method of claim 8, wherein measuring a streaming potential or streaming current includes measuring a streaming potential or streaming current at least ten Debye lengths from the surface.

15. The method of claim 8, wherein measuring a streaming potential or streaming current is done with reference to a location at least ten radii from a point at which the axis intersects the surface.

16. The method of claim 11, further comprising determining a current collection efficiency.

17. The method of claim 16, wherein determining current collection efficiency includes determining:

$$Eff = I_{meas}/(i_z \pi a^2)$$

wherein $I_{meas}$ is measured current;

$i_z$ is current density flowing from the surface; and a is the radius of the surface.

* * * * *